US00PP19180P2

(12) United States Plant Patent
Ramirez

(10) Patent No.: US PP19,180 P2
(45) Date of Patent: Sep. 2, 2008

(54) ***SOLENOSTEMON* PLANT NAMED 'BALCINSU'**

(50) Latin Name: *Solenostemon Scutellarioides*
Varietal Denomination: Balcinsu

(75) Inventor: Rolando Solano Ramirez, Dulce Nombre de Cartago (CR)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/809,818

(22) Filed: Jun. 1, 2007

(51) Int. Cl.
*A01H 5/00* (2006.01)

(52) U.S. Cl. ..... Plt./373

(58) Field of Classification Search ..... Plt./373
See application file for complete search history.

(56) References Cited

PUBLICATIONS

Canada Plant Breeders' Right application No. 07–5879 filed Apr. 12, 2007—not published when this IDS wa prepared.

*Primary Examiner*—Kent L Bell
(74) *Attorney, Agent, or Firm*—Audrey Charles

(57) ABSTRACT

A new and distinct cultivar of *Solenostemon* plant named 'Balcinsu', characterized by its red brown, green and yellow green-colored foliage and vigorous, upright growth habit.

1 Drawing Sheet

Latin name of genus and species of plant claimed: *Solenostemon scutellarioides.*
Variety denomination: 'Balcinsu'.

BACKGROUND OF THE INVENTION

The present invention relates to a new and distinct cultivar of *Solenostemon* plant botanically known as *Solenostemon scutellarioides* and hereinafter referred to by the cultivar name 'Balcinsu'.

The new cultivar originated in a controlled breeding program in Cartago, Costa Rica during January 2004. The objective of the breeding program was the development of *Solenostemon* cultivars with unique foliage coloration and leaf shape, upright growth habit, and good sun tolerance.

The new *Solenostemon* cultivar is the result of cross-pollination. The female (seed) parent of the new cultivar is 'Elfers', not patented, characterized by its deep purple, green, and magenta-colored foliage and upright growth habit. The male (pollen) parent of the new cultivar is from a Wizard™ bulk pollen mix, not patented, characterized by its green, red, magenta, yellow-green, and scarlet red foliage colors, zoned and solid foliage color patterns, and upright growth habit. The new cultivar was discovered and selected as a single flowering plant within the progeny of the above stated cross-pollination during November 2004 in a controlled environment at Cartago, Costa Rica.

Asexual reproduction of the new cultivar by terminal stem cuttings since November 2004 at Cartago, Costa Rica and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcinsu' as a new and distinct cultivar of *Solenostemon* plant:

1. Red brown, green and yellow green-colored foliage; and
2. Vigorous, upright growth habit.

Plants of the new cultivar differ from plants of the female parent primarily in foliage color and from plants of the male parent primarily in foliage color and growth habit. Plants of the new cultivar are not as compact as plants of the male parent.

Of the many commercially available *Solenostemon* cultivars known to the inventor, the most similar in comparison to the new cultivar is 'Volcano', not patented. However, in side by side comparisons, plants of the new cultivar differ from plants of 'Volcano' in the following characteristics:

1. Plants of the new cultivar have a foliage color different from plants of 'Volcano'; and
2. Plants of the new cultivar have a more deeply lobed leaf margin than plants of 'Volcano'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Balcinsu'. The plants were grown in 4.5 inch pots for 5 weeks in a greenhouse at West Chicago, Ill. Plants were given one pinch at transplant.

DETAILED BOTANICAL DESCRIPTION

Figure 1:
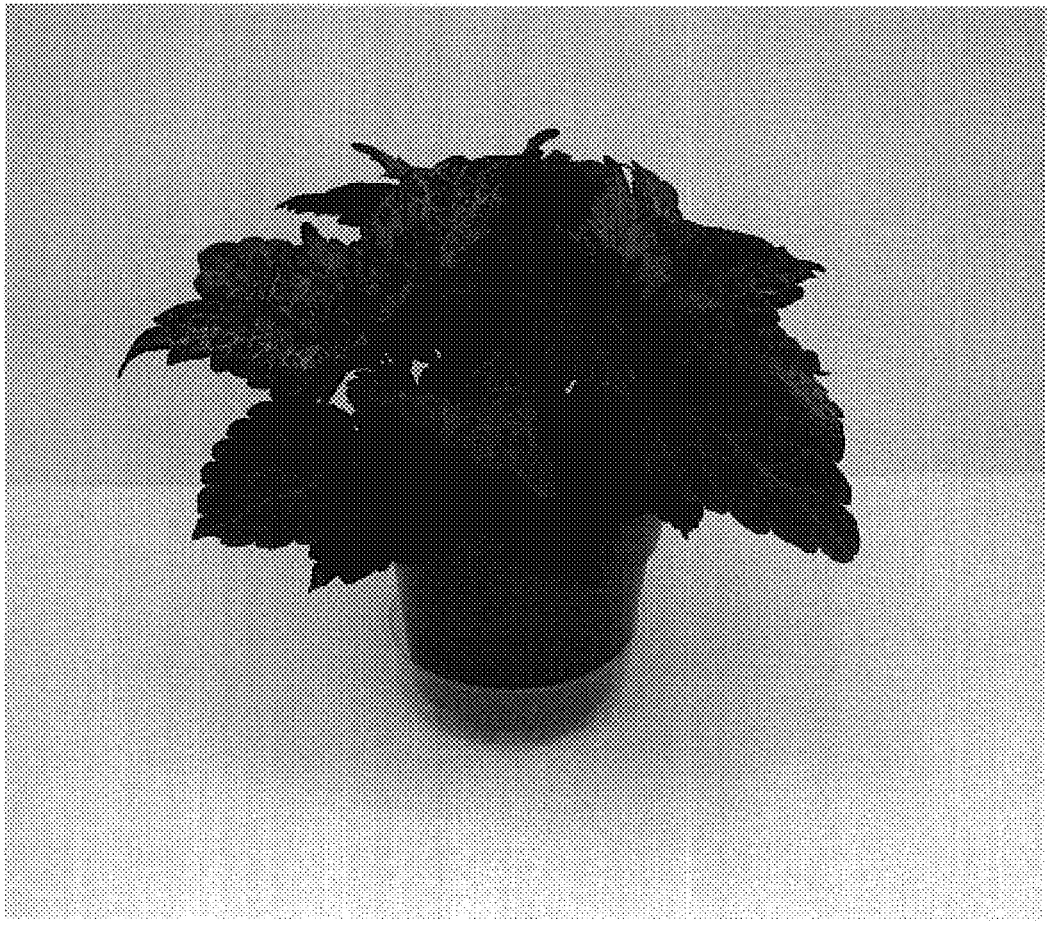
FIG. 1 illustrates a side view of the overall growth habit of 'Balcinsu'.
Figure 2:
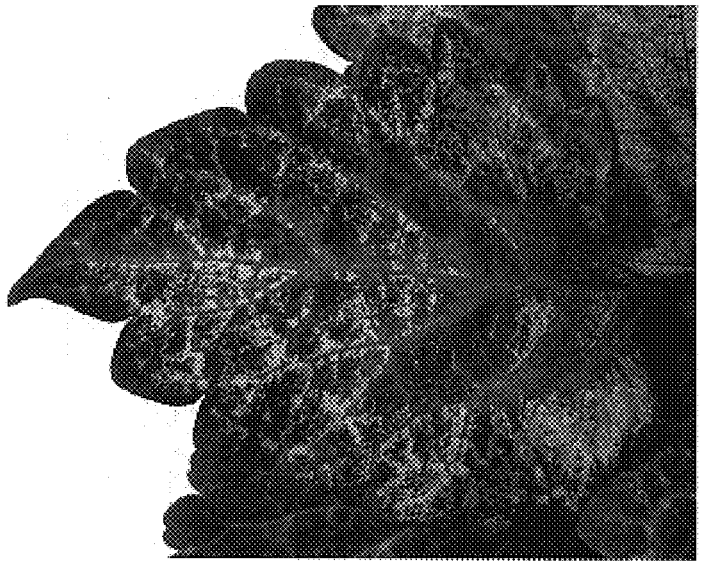
FIG. 2 illustrates a close-up view of an individual leaf of 'Balcinsu'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 19, 2007 between 1:00 p.m. and 3:00 p.m. under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 5 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Solenostemon scutellarioides* cultivar Balcinsu.

Parentage:

*Female parent.*—'Elfers', not patented.

*Male parent.*—Wizard™ bulk pollen mix, not patented.

Propagation:

*Type cutting.*—Terminal stem.

*Time to initiate roots.*—Approximately 4 to 6 days.

*Time to produce a rooted cutting.*—Approximately 21 to 24 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Vigorous, upright.

*Size.*—Height from soil level to top of plant plane: Approximately 12.2 cm. Width: Approximately 23.8 cm.

*Branching habit.*—Freely branching, pinching improves basal branching. Quantity of lateral branches per plant: Approximately 4.

*Branch.*—Strength: Strong. Shape: Square in cross section. Length of basal lateral branch: Approximately 9.8 cm. Diameter of basal lateral branch at central internode: Approximately 5.0 mm. Length of central internode of basal lateral branch: Approximately 2.0 cm. Texture: Densely pubescent. Pubescence color: 187B. Color of young and mature stems: 187A.

Foliage description:

*General description.*—Quantity of leaves per main stem: Approximately 6. Fragrance: None. Form: Simple. Arrangement: Opposite.

*Leaves.*—Aspect: Acute angle to stem; leaf blade transitions to an obtuse angle with age. Shape: Ovate. Margin: Crenate. Apex: Acute. Base: Attenuate. Venation pattern: Pinnate. Length of mature leaf: Approximately 9.0 cm. Width of mature leaf: Approximately 6.9 cm. Texture of upper surface: Rugose, sparsely pubescent. Texture of lower surface: Rugose, sparsely pubescent with dense pubescence on venation. Pubescence color: 187B. Color of upper surface of young foliage: Irregular central area of 184A; outward from central area has mottling of 137A with 150C surrounding venation, speckles throughout and margins of 187A, and venation of N186D. Color of lower surface of young and mature foliage: 187A with 187B surrounding venation and venation of N186D. Color of upper surface of mature foliage: Irregular central area of 184A; outward from central area has mottling of 137A with 145A to 145B surrounding venation, speckles throughout and margins of 187A, and venation of N186D. With age, speckles and margins of 187A become more pronounced.

*Petiole.*—Length: Approximately 2.1 cm. Width: Approximately 3.0 mm. Texture: Densely pubescent. Pubescence color: 187B. Color: N186D.

Flowering description: Flowers are ornamentally insignificant for this variety. No flowers were observed in this trial.

Seed and fruit production: Neither seed nor fruit production has been observed.

Disease and pest resistance: Resistance to pathogens and pests common to *Solenostemon* has not been observed.

What is claimed is:

1. A new and distinct cultivar of *Solenostemon* plant named 'Balcinsu', substantially as herein shown and described.

* * * * *